(12) United States Patent
Oh et al.

(10) Patent No.: US 8,030,239 B2
(45) Date of Patent: Oct. 4, 2011

(54) CATALYST FOR XYLENE ISOMERIZATION AND PROCESS FOR PREPARING THE SAME

(75) Inventors: Seung Hoon Oh, Seoul (KR); Sang Il Lee, Daejeon (KR); Kyeong Hak Seong, Daejeon (KR); Jong Hyung Lee, Daejeon (KR); Kyung Jong Oh, Daejeon (KR)

(73) Assignee: SK Energy Co., Ltd., Seoul (KR)

( * ) Notice: Subject to any disclaimer, the term of this patent is extended or adjusted under 35 U.S.C. 154(b) by 233 days.

(21) Appl. No.: 12/312,361

(22) PCT Filed: Nov. 16, 2007

(86) PCT No.: PCT/KR2007/005771
§ 371 (c)(1),
(2), (4) Date: May 5, 2009

(87) PCT Pub. No.: WO2008/060117
PCT Pub. Date: May 22, 2008

(65) Prior Publication Data
US 2010/0048381 A1    Feb. 25, 2010

(30) Foreign Application Priority Data

Nov. 17, 2006  (KR) .................. 10-2006-0113703
Nov. 7, 2007   (KR) .................. 10-2007-0113234

(51) Int. Cl.
*B01J 29/06*  (2006.01)
(52) U.S. Cl. ............... 502/63; 502/64; 502/66; 502/71
(58) Field of Classification Search .............. 502/63, 502/64, 66, 71
See application file for complete search history.

(56) References Cited

U.S. PATENT DOCUMENTS

| 4,377,718 A | * | 3/1983 | Sato et al. .................. 585/467 |
| 4,447,666 A | * | 5/1984 | McWilliams ............... 585/467 |
| 4,482,773 A |   | 11/1984 | Chu et al. |
| 4,547,472 A | * | 10/1985 | Van Nordstrand .......... 502/66 |
| 4,721,694 A | * | 1/1988 | Buss et al. .................. 502/66 |
| 4,939,110 A |   | 7/1990 | Sachtler et al. |
| 5,053,372 A | * | 10/1991 | Brownscombe ............. 502/60 |
| 5,300,695 A | * | 4/1994 | Radlowski .................. 568/697 |
| 6,518,472 B1 |  | 2/2003 | Feinstein et al. |
| 2003/0115855 A1 | * | 6/2003 | Miyoshi et al. ............. 60/284 |

FOREIGN PATENT DOCUMENTS

| CN | 1102360 A | 5/1995 |
| JP | 4346838 A | 12/1992 |
| JP | 6121932 A | 5/1994 |
| JP | 200042418 A | 2/2000 |

OTHER PUBLICATIONS

International Search Report for International Application No. PCT/KR2007/005771 dated Feb. 20, 2008.

* cited by examiner

*Primary Examiner* — Elizabeth Wood
(74) *Attorney, Agent, or Firm* — Abelman, Frayne & Schwab

(57) ABSTRACT

Disclosed herein is a catalyst for xylene isomerization, including: a carrier including a zeolite, having a molar ratio of silica to alumina of 20~100, impregnated with or mixed with a metal salt (I) having an amount of a metal component of 0.05~5.0 wt % relative to a zeolite, and an inorganic binder, in which an amount of the zeolite is 10~90 wt % based on the total amount of the carrier, wherein the carrier is supported with a VIII group metal such that an amount of the VIII group metal is 0.001~3.0 wt % based on a total amount of the catalyst, or is supported with the VII group metal additionally supported with tin, bismuth or lead such that an amount of the tin, bismuth or lead is 0.01-5.0 wt % based on the total amount of the catalyst, and a method of producing the catalyst. The catalyst for xylene isomerization is advantageous in that, when xylene or C8 aromatic compounds are isomerized using the catalyst, the ethylbenzene conversion is increased while the xylene loss is decreased, compared to conventional technologies.

12 Claims, 2 Drawing Sheets

US 8,030,239 B2

CATALYST FOR XYLENE ISOMERIZATION AND PROCESS FOR PREPARING THE SAME

CROSS-REFERENCE TO RELATED APPLICATIONS

This application is a Section 371 National Phase of PCT/KR2007/005771, filed Nov. 16, 2007, which claims the priority benefit of Korean Application 10-2006-0113703, filed Nov. 17, 2006 and Korean Application 10-2007-0113234, filed Nov. 7, 2007.

TECHNICAL FIELD

The present invention relates to a catalyst for xylene isomerization and a method of producing the catalyst, and, more particularly, to a catalyst for xylene isomerization produced by impregnating a zeolite with a metal salt or directly mixing a zeolite with a metal salt, and a method of producing the catalyst.

BACKGROUND ART

A C8 aromatic compound is a very important raw material in the petrochemical industry. Examples of C8 aromatic compounds include xylenes, such as meta-xylene, paraxylene, ortho-xylene, and ethylbenzene. In particular, para-xylene is used as a main raw material for polyester fiber, and is separated from a C8 aromatic compound, which is commercially produced by reforming and cracking naphtha.

General methods of separating paraxylene from a C8 aromatic compound include the steps of separating paraxylene from the C8 aromatic compound through a unit process for the crystallization, adsorption and separation of the C8 aromatic compound, converting raffinate, which is the residual C8 aromatic compound, into a paraxylene-containing C8 aromatic compound by introducing the raffinate into an isomerization unit for forming paraxylene, and additionally separating and collecting paraxylene from the paraxylene-containing C8 aromatic compound by refluxing the paraxylene-containing C8 aromatic compound to a separation unit.

Generally, a C8 aromatic compound, which is produced by reforming and cracking naphtha, includes ethylbenzene, having a benzene ring bonded with one ethyl group, and xylene, having a benzene ring bonded with two methyl groups. When the C8 aromatic compound is isomerized, a disproportionation reaction, in which one methyl group of xylene is bonded to another xylene, thus producing one toluene and one trimethylbenzene, occurs. Therefore, the disproportion reaction incurs the loss of xylene during the isomerization process. 1% xylene loss has a cumulative economic effect of several billions to several tens of billions of/year on petrochemical companies, depending on the scale thereof.

In a process for producing paraxylene or ortho-xylene, isomerization catalysts generally serve to facilitate the isomerization reaction between xylene isomers, and serve to convert ethylbenzene into benzene through a dealkylation reaction, or convert the ethylbenzene into a xylene isomer through the isomerization reaction. A zeolite catalyst supported with a metal component of the VIII group of the periodic table is currently used as a commercial isomerization catalyst.

Examples of conventional zeolite catalysts supported with various metal components and used as catalysts for isomerizing xylene and converting ethylbenzene are as follows.

U.S. Pat. No. 4,939,110 discloses a method of producing a catalyst for isomerizing a C8 aromatic compound, comprising the steps of mixing an inorganic oxide binder, such as gamma-aluminum, with a pentasil zeolite, such as ZSM-5, such that the amount of the zeolite is 1~20 wt %, to form a carrier, and supporting the carrier with 0.01~2 wt % of a VIII group metal, such as platinum, and lead such that the amount of lead is 2~10 times the amount of the VIII group metal. In the method, 80~100% of the VIII group metal and 60~100% of the lead are supported on the inorganic oxide binder, rather than the zeolite. As the result of isomerizing a C8 aromatic compound containing about 10 wt % of ethylbenzene on the catalyst, it was found that xylene loss is 0.8~1.5 wt % when ethylbenzene conversion is 65 wt %. However, the method is problematic in that xylene loss is large compared to ethylbenzene conversion, and the lead content is very high.

Furthermore, U.S. Pat. No. 4,482,773 (Examples 1 to 3) discloses a method of a catalyst for isomerizing xylene and converting ethylbenzene, in which the catalyst is produced by impregnating ZSM-5, including no binder, with platinum and magnesium. In the method, in the case of the catalyst produced by impregnating the ZSM-5 into 2.4 wt % of a magnesium nitrate solution and then impregnating the ZSM-5 with 0.1 wt % of platinum, xylene loss is about 2.7 wt % when ethylbenzene conversion is 70 wt %.

The above conventional methods are problematic in that the loss of xylene must occur at a constant level in order to obtain a constant conversion rate of ethylbenzene.

DISCLOSURE

Technical Problem

In order to overcome the above problems occurring in the prior art, the present inventors have conducted continuous research. As a result, they have found methods of preventing side reactions and reducing xylene loss by controlling the acid site of a zeolite while impregnating or mixing the zeolite with a metal salt component. Based on the finding, the present invention was completed.

Accordingly, the present invention provides a catalyst for isomerizing xylene, which can maximize the ethylbenzene conversion and minimize the xylene loss during the isomerization reaction of a C8 aromatic compound, and a method of producing the catalyst.

Technical Solution

In an aspect, the present invention provides a catalyst for xylene isomerization, comprising a carrier including a zeolite, having a molar ratio of silica to alumina of 20~100, impregnated with or mixed with a metal salt (I) having an amount of a metal component of 0.05~5.0 wt % relative to a zeolite, and an inorganic binder, in which an amount of the zeolite is 10~90 wt % based on the total amount of the carrier, wherein the carrier is supported with a VIII group metal such that an amount of the VIII group metal is 0.001~3.0 wt % based on a total amount of the catalyst, or is supported with the VIII group metal additionally supported with tin, bismuth or lead such that an amount of the tin, bismuth or lead is 0.01~5.0 wt % based on the total amount of the catalyst.

Advantageous Effects

The catalyst for xylene isomerization produced using the method according to the present invention is advantageous in that the ethylbenzene conversion is high and the xylene loss is low compared to the catalyst produced using a conventional method.

BEST MODE

Figure 1:
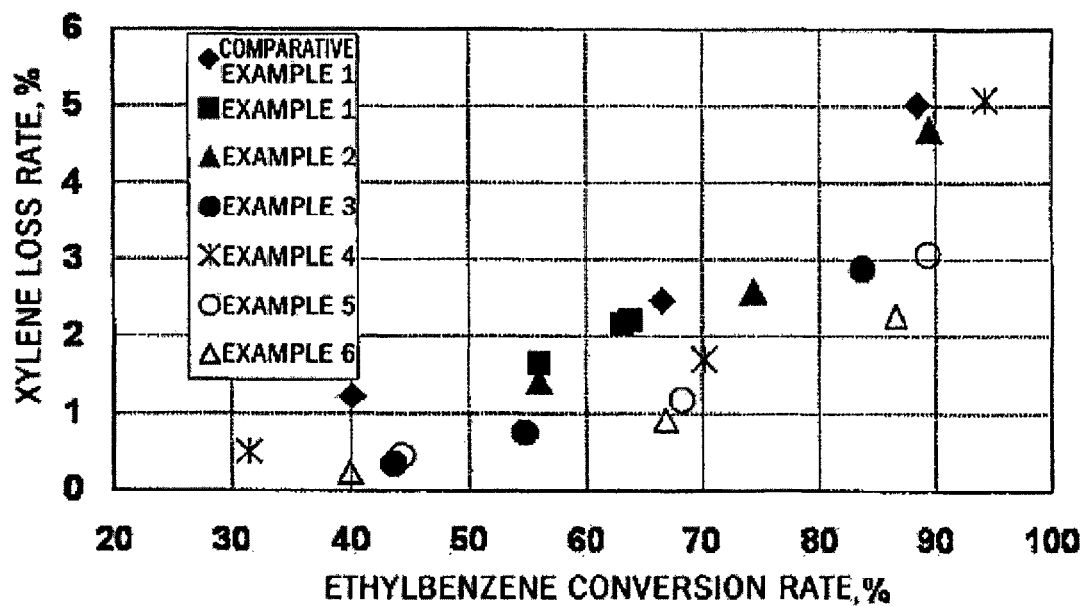
FIG. 1 is a graph showing the relationship between the xylene loss and the ethylbenzene conversion in the isomerization reaction using a catalyst produced in Examples 1 to 6 according to the present invention.

Hereinafter, the present invention will be described in more detail.

As described above, the present invention provides a catalyst for xylene isomerization and a method of producing the catalyst. The present invention, unlike conventional technologies, is characterized in that a zeolite is impregnated or directly mixed with a metal salt (I), such as calcium acetylacetonate, so that the acid site of the zeolite is controlled, thereby minimizing the xylene loss attributable to the disproportionation of xylene.

Further, the present invention is characterized in that the zeolite is ion-exchanged with a metal salt (II), such as magnesium nitrate, and is then impregnated or directly mixed with the metal salt (I), thus improving the structural characteristics of the zeolite.

A method of producing a catalyst for xylene isomerization according to an embodiment of the present invention includes: supporting a zeolite having a molar ratio of silica to alumina of 20~100 with a metal salt (I) having an amount of a metal component of 0.05~5.0 wt % relative to the zeolite; mixing the zeolite supported with the metal salt (I) with an inorganic binder to form a mixture powder so that the weight ratio of the zeolite to the mixture powder is 10~90 wt %; and supporting the mixture powder with a VIII group metal such that the amount of the VIII group metal is 0.001~3.0 wt % based on the total amount of the catalyst, or supporting the mixture powder with the VIII group metal, additionally supported with tin, bismuth or lead such that the amount of the tin, bismuth or lead is 0.01~5.0 wt % based on the total amount of the catalyst.

Further, a method of producing a catalyst for xylene isomerization according to another embodiment of the present invention includes: directly mixing a metal salt (I), having an amount of a metal component of 0.05~5.0 wt % relative to a zeolite, with the zeolite, having a molar ratio of silica to alumina of 20~100, and an inorganic binder to form a mixture powder so that the weight ratio of the zeolite to the mixture powder is 10~90 wt %; and supporting the mixture powder with a VIII group metal such that the amount of the VIII group metal is 0.001~3.0 wt % based on the total amount of the catalyst, or supporting the mixture powder with the VIII group metal additionally supported with tin, bismuth or lead such that the amount of the tin, bismuth or lead is 0.01~5.0 wt % based on the total amount of the catalyst.

In the method of producing a catalyst for xylene isomerization according to the present invention, the zeolite may be ZSM-5, ZSM-8, ZSM-11, ZSM-12, ZSM-23, ZSM-35, ZSM-48, SSZ-46, TS-1, TS-2, mordenite, or Beta, and more preferably ZSM-5.

The metal salt (I) may be selected from the group consisting of beryllium nitrate, beryllium halide, beryllium acetate, beryllium naphthenate, beryllium gluconate, beryllium citrate, beryllium acetylacetonate, beryllium carbonate, beryllium formate, beryllium sulfate, beryllium hydroxide, magnesium nitrate, magnesium halide, magnesium acetate, magnesium naphthenate, magnesium gluconate, magnesium citrate, magnesium acetylacetonate, magnesium carbonate, magnesium formate, magnesium sulfate, magnesium hydroxide, calcium nitrate, calcium halide, calcium acetate, calcium naphthenate, calcium gluconate, calcium citrate, calcium acetylacetonate, calcium carbonate, calcium formate, calcium sulfate, calcium hydroxide, barium nitrate, barium halide, barium acetate, barium naphthenate, barium gluconate, barium citrate, barium acetylacetonate, barium carbonate, barium formate, barium sulfate, and barium hydroxide. Preferably, the zeolite is impregnated or directly mixed using the acetylacetonate, carbonate as a precursor. Most preferably, the zeolite is impregnated or directly mixed using the calcium acetylacetonate or calcium carbonate as a precursor.

The metal salt (I) is dissolved in a solvent, such as distilled water, tetrahydrofuran (THF), dimethylformamide (DMF), dimethylacetamide (DMAC), dimethylsulfoxide (DMSO), or the like, or a mixed solvent thereof, and is then supported in an ammonium or hydrogen type zeolite or is directly mixed with the zeolite without using the solvent. The metal salt (I) may have an amount of a metal component of 0.05~5.0 wt % relative to a zeolite, and preferably 0.1~3.0 wt %. When the amount of the metal component relative to the zeolite is below 0.05 wt %, there is a problem in that the xylene loss is increased. In contrast, when the amount of the metal component relative to the zeolite is above 5.0 wt %, there is a problem in that the activity of the catalyst is rapidly decreased.

In the present invention, the ammonium or hydrogen type zeolite may be used.

The zeolite must be mixed with at least one inorganic binder. The inorganic binder may be selected from the group consisting of silica, silica-alumina, alumina, aluminum phosphate, bentonite, kaolin, clinoptilolite, and montmorillonite. Preferably, the inorganic binder may be silica, silica-alumina, and alumina amorphous inorganic oxide, and most preferably, in order to exhibit optimal catalyst performance, gamma-alumina or silica.

When the inorganic binder is combined with the zeolite impregnated with the metal salt (I), it is preferred that the amount of the zeolite be 10~90 wt % based on the total amount of mixture powder.

The VIII group metal precursor may be used in the form of chloride, nitride, or ammonium. It is preferred that the amount of the VIII group metal be 0.001~3.0 wt % based on the total amount of the catalyst. When the amount of the VIII group metal is below 0.001 wt %, there is a problem in that the dealkylation reaction of ethylbenzene is weakened, thus decreasing the conversion rate of ethylbenzene. In contrast, when the amount of the VIII group metal is above 3.0 wt %, there is a problem in that the function of the VIII group metal is excessively strengthened, thus producing a large amount of low molecular weight hydrocarbons (C1~C4) and naphthene-based compounds.

Further, as precursors of the tin, bismuth or lead, chlorides and nitrides thereof may be used. It is preferred that the amount of the tin, bismuth or lead be 0.01~5.0 wt % based on the total amount of the catalyst. When the amount of the tin, bismuth or lead is below 0.01 wt %, there is a problem in that it is difficult to control the hydrogenation function of platinum, and thus xylene is lost in side reactions. In contrast, when the amount of the tin, bismuth or lead is above 5.0 wt %, there is a problem in that the hydrogenation function of platinum is excessively suppressed, thus excessively decreasing the activity of catalyst.

Meanwhile, before the supporting the zeolite with the metal salt (I), a process for mixing a metal salt (II), such as magnesium nitrate, with the zeolite having a molar ratio of silica to alumina of 20~100, to conduct an ion-exchange reaction may be performed. The ion-exchange reaction may be conducted at a temperature of 30~250° C., preferably 50~200° C. As the ion-exchange reaction temperature is increased, the concentration of the metal salt (II) that is ion-exchanged with the zeolite is increased. When the ion-exchange reaction temperature is below 30° C., there is a problem in that the ion-exchange reaction is not conducted. In contrast, when the ion-exchange reaction temperature is above 250° C., there is a problem in that the concentration of the metal salt (II) is rapidly increased, and thus the activity of the catalyst is rapidly decreased.

The metal salt (II) may be selected from the group consisting of beryllium nitrate, beryllium halide, beryllium acetate, beryllium citrate, beryllium gluconate, beryllium carbonate, beryllium formate, beryllium sulfate, beryllium hydroxide, magnesium nitrate, magnesium halide, magnesium acetate, magnesium citrate, magnesium gluconate, magnesium carbonate, magnesium formate, magnesium sulfate, magnesium hydroxide, calcium nitrate, calcium halide, calcium acetate, calcium citrate, calcium gluconate, calcium carbonate, calcium formate, calcium sulfate, calcium hydroxide, barium nitrate, barium halide, barium acetate, barium citrate, barium gluconate, barium carbonate, barium formate, barium sulfate, barium hydroxide, and mixtures thereof. In this case, the total amount of magnesium, beryllium, calcium and barium may be 0.001~3.0 wt %, and preferably 0.01~2.0 wt %, based on the amount of zeolite. When the total amount of magnesium, beryllium, calcium and barium is below 0.001 wt %, there is a problem in that the loss of xylene is increased. In contrast, when the total amount thereof is above 3.0 wt %, there is a problem in that the activity of the catalyst is rapidly decreased.

MODE FOR INVENTION

A better understanding of the present invention may be obtained through the following examples, which are set forth to illustrate, but are not to be construed as the limit of the present invention.

COMPARATIVE EXAMPLE 1

An ammonium type ZSM-5 having a molar ratio of silica to alumina of 50 was formed into a mixture powder such that the amount of the ZSM-5 relative to the mixture powder was 50 wt %, using alumina as an inorganic binder. Subsequently, this mixture powder was supported with a mixed acid solution of 0.3 wt % of platinum and 1.5 wt % of tin to produce a catalyst. Here, chloroplatinic acid was used as a precursor of platinum, and tin chloride was used as a precursor of tin. The produced catalyst was calcined at a temperature of 500° C.

In a xylene isomerization reaction, a C8 aromatic compound, including 80~97 wt % of a mixture of ortho-xylene and meta-xylene, from which paraxylene was removed, and 3~20 wt % of ethylbenzene, was used as a reactant, and the C8 aromatic compound was introduced into a small-sized stainless steel reactor having an inner diameter of 1 inch and a length of 30 cm. The xylene isomerization reaction was conducted under conditions of the presence of 1.0 ~5.0 g of the catalyst, a reaction temperature of 300~460° C., a reaction pressure of 5~30 kg/cm², a molar ratio of hydrogen to hydrocarbon of 2.0~10.0, and a weight hourly space velocity (WHSV) of liquid reactants of 5.0~30.0 hr$^{-1}$.

Figure 2:
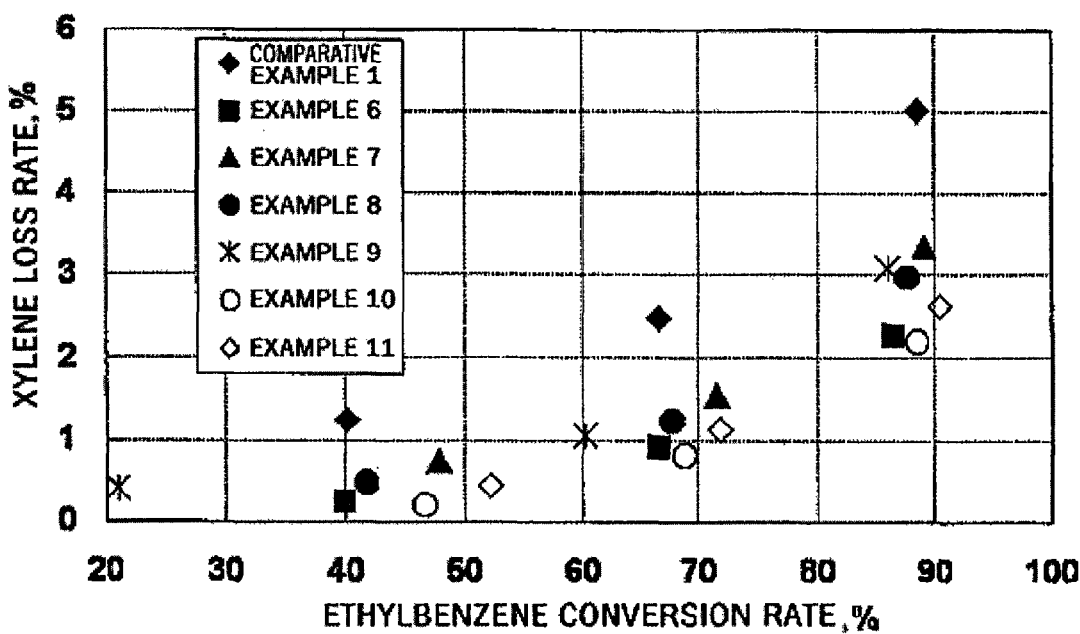
FIG. 2 is a graph showing the relationship between the xylene loss and the ethylbenzene conversion in the isomerization reaction using a catalyst produced in Examples 7 to 11 according to the present invention.
Figure 3:
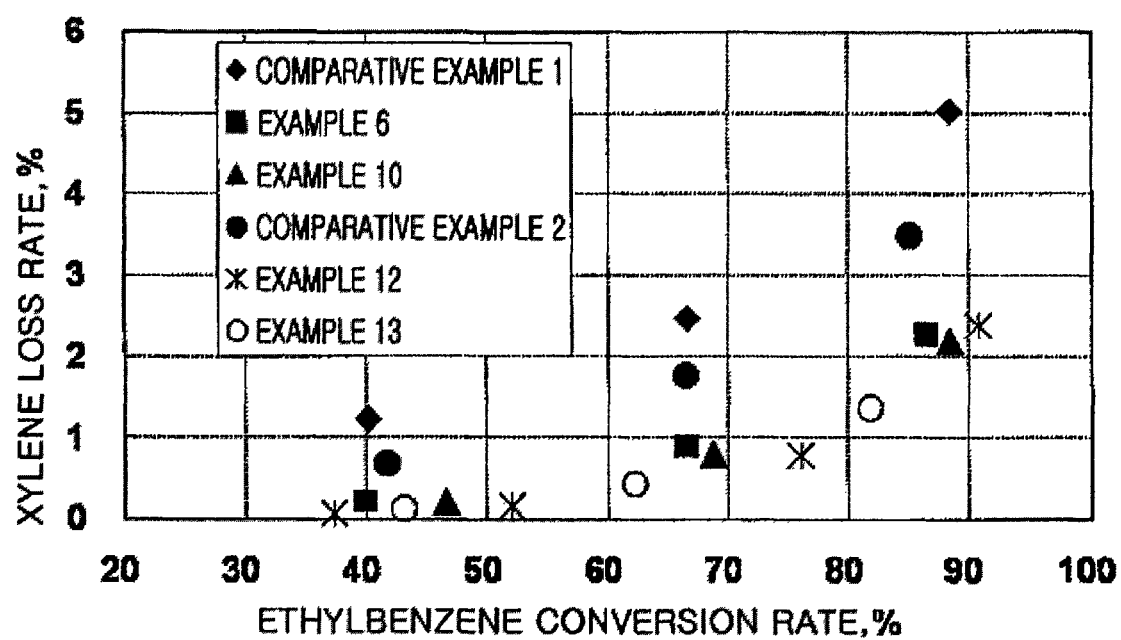
FIG. 3 is a graph showing the relationship between the xylene loss and the ethylbenzene conversion in the isomerization reaction using a catalyst produced in Examples 12 and 13 according to the present invention.

The results of the xylene isomerization reaction are shown in FIGS. 1, 2, and 3.

EXAMPLE 1

Calcium nitrate was dissolved in distilled water such that the amount of Ca was 1.0 wt % based on the amount of ZSM-5, the dissolved calcium nitrate was supported in ammonium type ZSM-5 having a molar ratio of silica to alumina of 50, and then the ZSM-5 supported with calcium nitrate was calcined at a temperature of 500° C. Subsequently, the calcined ZSM-5 was formed into a mixture powder using alumina as a binder such that the weight ratio of the ZSM-5 in the mixture powder was 70%. Subsequently, this mixture powder was supported with a mixed acid solution of 0.3 wt % of platinum and 1.5 wt % of tin to produce a catalyst. Here, chloroplatinic acid was used as a precursor of platinum, and tin chloride was used as a precursor of tin. The produced catalyst was calcined at a temperature of 500° C.

The xylene isomerization reaction was conducted as in Comparative Example 1, and the result thereof is shown in FIG. 1. From FIG. 1, it can be seen that the catalyst obtained in the Example has better catalytic performance than the conventional catalyst obtained in Comparative Example 1.

EXAMPLE 2

Calcium naphthenate was dissolved in dimethylformamide (DMF) such that the amount of Ca was 0.5 wt % based on the amount of ZSM-5, the dissolved calcium naphthanate was supported in ammonium type ZSM-5 having a molar ratio of silica to alumina of 50, and then the ZSM-5 supported with calcium naphthenate was calcined at a temperature of 550° C. Subsequently, the calcined ZSM-5 was formed into a mixture powder using alumina as a binder such that the weight ratio of the ZSM-5 in the mixture powder was 70%. Subsequently, this mixture powder was supported with a mixed acid solution of 0.3 wt % of platinum and 1.5 wt % of tin to produce a catalyst. Here, chloroplatinic acid was used as a precursor of platinum, and tin chloride was used as a precursor of tin. The produced catalyst was calcined at a temperature of 500° C.

The xylene isomerization reaction was conducted as in Comparative Example 1, and the result thereof is shown in FIG. 1.

EXAMPLE 3

Calcium gluconate was dissolved in distilled water such that the amount of Ca was 1.0 wt % based on the amount of ZSM-5, the dissolved calcium gluconate was supported in ammonium type ZSM-5 having a molar ratio of silica to alumina of 50, and then the ZSM-5 supported with calcium gluconate was calcined at a temperature of 500° C. Subsequently, the calcined ZSM-5 was formed into a mixture powder using alumina as a binder such that the weight ratio of the ZSM-5 in the mixture powder was 70%. Subsequently, this mixture powder was supported with a mixed acid solution of 0.3 wt % of platinum and 1.4 wt % of tin to produce a catalyst. Here, chloroplatinic acid was used as a precursor of platinum, and tin chloride was used as a precursor of tin. The produced catalyst was calcined at a temperature of 550° C.

The xylene isomerization reaction was conducted as in Comparative Example 1, and the result thereof is shown in FIG. 1.

EXAMPLE 4

Calcium citrate was mixed with ammonium type ZSM-5, having a molar ratio of silica to alumina of 50, such that the amount of Ca was 0.5 wt % based on the amount of ZSM-5. Subsequently, the mixture thereof was mixed with alumina to form a mixture powder such that the weight ratio of the ZSM-5 in the mixture powder was 70%. Subsequently, this mixture powder was supported with a mixed acid solution of 0.2 wt % of platinum and 1.0 wt % of tin to produce a catalyst. Here, chloroplatinic acid was used as the precursor of platinum, and tin chloride was used as a precursor of tin. The produced catalyst was calcined at a temperature of 450° C.

The xylene isomerization reaction was conducted as in Comparative Example 1, and the result thereof is shown in FIG. 1.

EXAMPLE 5

Calcium carbonate was mixed with ammonium type ZSM-5 having a molar ratio of silica to alumina of 50 such that the amount of Ca was 0.5 wt % based on the amount of ZSM-5. Subsequently, the mixture thereof was mixed with alumina to form a mixture powder such that the weight ratio of the ZSM-5 in the mixture powder was 70%. Subsequently, this mixture powder was supported with a mixed acid solution of 0.1 wt % of platinum and 1.0 wt % of tin to produce a catalyst. Here, chloroplatinic acid was used as a precursor of platinum, and tin chloride was used as a precursor of tin. The produced catalyst was calcined at a temperature of 500° C.

The xylene isomerization reaction was conducted as in Comparative Example 1, and the result thereof is shown in FIG. 1.

EXAMPLE 6

Calcium acetylacetonate was dissolved in dimethylformamide (DMF) such that the amount of Ca was 1.0 wt % based on the amount of ZSM-5, the dissolved calcium acetylacetonate was supported in ammonium type ZSM-5 having a molar ratio of silica to alumina of 50, and then the ZSM-5 supported with calcium acetylacetonate was calcined at a temperature of 500° C. Subsequently, the calcined ZSM-5 was formed into a mixture powder using alumina as a binder such that the weight ratio of the ZSM-5 in the mixture powder was 70%. Subsequently, this mixture powder was supported with a mixed acid solution of 0.3 wt % of platinum and 1.5 wt % of tin to produce a catalyst. Here, chloroplatinic acid was used as a precursor of platinum, and tin chloride was used as a precursor of tin. The produced catalyst was calcined at a temperature of 550° C.

The xylene isomerization reaction was conducted as in Comparative Example 1, and the results thereof are shown in FIGS. 1, 2 and 3.

EXAMPLE 7

Magnesium acetylacetonate was dissolved in dimethylformamide (DMF) such that the amount of Mg was 0.9 wt % based on the amount of ZSM-5, the dissolved magnesium acetylacetonate was supported in ammonium type ZSM-5 having a molar ratio of silica to alumina of 50, and then the ZSM-5 supported with magnesium acetylacetonate was calcined at a temperature of 500° C. Subsequently, the calcined ZSM-5 was formed into a mixture powder using alumina as a binder such that the weight ratio of the ZSM-5 in the mixture powder was 70%. Subsequently, this mixture powder was supported with a mixed acid solution of 0.3 wt % of platinum and 1.5 wt % of tin to produce a catalyst. Here, chloroplatinic acid was used as a precursor of platinum, and tin chloride was used as a precursor of tin. The produced catalyst was calcined at a temperature of 500° C.

The xylene isomerization reaction was conducted as in Comparative Example 1, and the result thereof is shown in FIG. 2.

EXAMPLE 8

Barium acetylacetonate was dissolved in dimethylformamide (DMF) such that the amount of Ba was 1.2 wt % based on the amount of ZSM-5, the dissolved barium acetylacetonate was supported in ammonium type ZSM-5 having a molar ratio of silica to alumina of 50, and then the ZSM-5 supported with barium acetylacetonate was calcined at a temperature of 500° C. Subsequently, the calcined ZSM-5 was formed into a mixture powder using alumina as a binder such that the weight ratio of the ZSM-5 in the mixture powder was 70%. Subsequently, this mixture powder was supported with a mixed acid solution of 0.2 wt % of platinum and 1.0 wt % of tin to produce a catalyst. Here, chloroplatinic acid was used as a precursor of platinum, and tin chloride was used as a precursor of tin. The produced catalyst was calcined at a temperature of 450° C.

The xylene isomerization reaction was conducted as in Comparative Example 1, and the result thereof is shown in FIG. 2.

EXAMPLE 9

Beryllium acetylacetonate was dissolved in dimethylformamide (DMF) such that the amount of Be was 0.3 wt % based on the amount of ZSM-5, the dissolved beryllium acetylacetonate was supported in hydrogen type ZSM-5 having a molar ratio of silica to alumina of 50, and then the ZSM-5 supported with beryllium acetylacetonate was calcined at a temperature of 500° C. Subsequently, the calcined ZSM-5 was formed into a mixture powder using alumina as a binder such that the weight ratio of the ZSM-5 in the mixture powder was 70%. Subsequently, this mixture powder was supported with a mixed acid solution of 0.3 wt % of platinum and 1.5 wt % of tin to produce a catalyst. Here, chloroplatinic acid was used as a precursor of platinum, and tin chloride was used as a precursor of tin. The produced catalyst was calcined at a temperature of 500° C.

The xylene isomerization reaction was conducted as in Comparative Example 1, and the result thereof is shown in FIG. 2.

EXAMPLE 10

Calcium acetylacetonate (wherein the amount of Ca was 1.0 wt % based on the amount of ZSM-5), ammonium type ZSM-5 (wherein the molar ratio of silica to alumina was 50), and alumina, serving as a binder, were simultaneously mixed with each other, and thus formed into a mixture powder. In this case, the mixture powder was formed such that the weight ratio of the ZSM-5, mixed with the Ca, in the mixture powder was 70%. Subsequently, this mixture powder was supported with a mixed acid solution of 0.3 wt % of platinum and 1.5 wt % of tin to produce a catalyst. Here, chloroplatinic acid was used as a precursor of platinum, and tin chloride was used as a precursor of tin. The produced catalyst was calcined at a temperature of 450° C.

The xylene isomerization reaction was conducted as in Comparative Example 1, and the results thereof are shown in FIGS. 2 and 3.

EXAMPLE 11

Calcium acetylacetonate (the amount of Ca was 0.8 wt % based on the amount of ZSM-5), hydrogen type ZSM-5 (the molar ratio of silica to alumina was 50), and alumina, serving as a binder, were simultaneously mixed with each other, and thus formed into a mixture powder. In this case, the mixture powder was formed such that the weight ratio of the ZSM-5, mixed with the Ca, in the mixture powder was 70%. Subsequently, this mixture powder was supported with 0.2 wt % of palladium to produce a catalyst. Here, palladium nitrate was used as a precursor of palladium. The produced catalyst was calcined at a temperature of 500° C.

The xylene isomerization reaction was conducted as in Comparative Example 1, and the result thereof is shown in FIG. 2.

COMPARATIVE EXAMPLE 2

Magnesium nitrate was dissolved in distilled water such that the amount of Mg was 0.5 wt % based on the amount of ZSM-5, the dissolved magnesium nitrate was mixed with ammonium type ZSM-5 having a molar ratio of silica to alumina of 50 and then ion-exchanged at a temperature of 85° C., and then the ion-exchanged ZSM-5 was calcined at a temperature of 500° C. Subsequently, the calcined ZSM-5 was formed into a mixture powder using alumina as a binder such that the weight ratio of the ZSM-5 in the mixture powder was 70%. Subsequently, this mixture powder was supported with a mixed acid solution of 0.2 wt % of platinum and 1.0 wt % of tin to produce a catalyst. Here, chloroplatinic acid was used as a precursor of platinum, and tin chloride was used as a precursor of tin. The produced catalyst was calcined at a temperature of 500° C.

The xylene isomerization reaction was conducted as in Comparative Example 1, and the result thereof is shown in FIG. 3.

EXAMPLE 12

Magnesium nitrate was dissolved in distilled water such that the amount of Mg was 1.0 wt % based on the amount of ZSM-5, the dissolved magnesium nitrate was mixed with ammonium type ZSM-5 having a molar ratio of silica to alumina of 50 and thus ion-exchanged at a temperature of 85° C., and then the ion-exchanged ZSM-5 was calcined at a temperature of 500° C. Subsequently, the Mg ion-exchanged ZSM-5 was mixed with calcium acetylacetonate such that the amount of Ca was 0.5 wt % based on the amount of the ZSM-5. Thereafter, the calcium acetylacetonate-mixed ZSM-5 was formed into a mixture powder using alumina as a binder such that the weight ratio of the ZSM-5, mixed with the Ca, in the mixture powder was 70%. Subsequently, this mixture powder was supported with a mixed acid solution of 0.03 wt % of platinum and 0.5 wt % of tin to produce a catalyst. Here, chloroplatinic acid was used as a precursor of platinum, and tin chloride was used as a precursor of tin. The produced catalyst was calcined at a temperature of 500° C.

The xylene isomerization reaction was conducted as in Comparative Example 1, and the result thereof is shown in FIG. 3.

EXAMPLE 13

Magnesium nitrate was dissolved in distilled water such that the amount of Mg was 2.0 wt % based on the amount of ZSM-5, the dissolved magnesium nitrate was mixed with ammonium type ZSM-5 having a molar ratio of silica to alumina of 50 and thus ion-exchanged at a temperature of 85° C., and then the ion-exchanged ZSM-5 was calcined at a temperature of 500° C. Subsequently, the Mg ion-exchanged ZSM-5 was mixed with calcium acetylacetonate such that the amount of Ca was 0.5 wt % based on the amount of the ZSM-5. Thereafter, the calcium acetylacetonate-mixed ZSM-5 was formed into a mixture powder using alumina as a binder such that the weight ratio of the ZSM-5, mixed with the Ca, in the mixture powder was 70%. Subsequently, this mixture powder was supported with a mixed acid solution of 0.03 wt % of platinum and 0.5 wt % of tin to produce a catalyst. Here, chloroplatinic acid was used as a precursor of platinum, and tin chloride was used as a precursor of tin. The produced catalyst was calcined at a temperature of 550° C.

The xylene isomerization reaction was conducted as in Comparative Example 1, and the result thereof is shown in FIG. 3.

From the results shown in FIGS. 1, 2 and 3, it can be seen that the catalyst impregnated or directly mixed with metal salt according to the present invention has a high ethylbenzene conversion and a low xylene loss compared to conventional catalysts, and particularly, the catalyst produced using calcium acetylacetonate and calcium carbonate as a metal salt (I) has excellent catalytic performance compared to other catalysts.

The invention claimed is:

1. A method of producing a catalyst for xylene isomerization, comprising the steps of:
   (i) mixing a metal salt (I) having an amount of a metal component of 0.05~5.0 wt % relative to a zeolite with the zeolite having a molar ratio of silica to alumina of 20~100 and an inorganic binder to form a mixture powder so that an amount of the zeolite based on the total amount of the powder mixture is 10~90 wt %; and
   (ii) supporting the mixture powder with a VIII group metal such that an amount of the VIII group metal is 0.001~3.0 wt % based on a total amount of the catalyst, or supporting the mixture powder with the VIII group metal additionally supported with tin, bismuth or lead such that an amount of the tin, bismuth or lead is 0.01~5.0 wt % based on the total amount of the catalyst,
   wherein the zeolite is selected from the group consisting of ZSM-5, ZSM-8, ZSM-11, ZSM-12, ZSM-23, ZSM-35, ZSM-48, SSZ-46, TS-1, TS-2, mordenite, and Beta, and
   the metal salt (I) is selected from consisting of beryllium nitrate, beryllium halide, beryllium acetate, beryllium naphthenate, beryllium gluconate, beryllium citrate, beryllium acetylacetonate, beryllium carbonate, beryllium formate, beryllium sulfate, beryllium hydroxide, magnesium nitrate, magnesium halide, magnesium acetate, magnesium naphthenate, magnesium gluconate, magnesium citrate, magnesium acetylacetonate, magnesium carbonate, magnesium formate, magnesium sulfate, magnesium hydroxide, calcium nitrate, calcium halide, calcium acetate, calcium naphthenate, calcium gluconate, calcium citrate, calcium acetylacetonate, calcium carbonate, calcium formate, calcium sulfate, calcium hydroxide, barium nitrate, barium halide, barium acetate, barium naphthenate, barium gluconate, barium citrate, barium acetylacetonate, barium carbonate, barium formate, barium sulfate, and barium hydroxide.

2. The method of producing a catalyst for xylene isomerization according to claim 1, wherein the step of mixing the metal salt (I) with the zeolite and the inorganic binder to form the mixture powder is performed sequentially or simultaneously.

3. The method of producing a catalyst for xylene isomerization according to claim 1, further comprising, before the step of mixing the metal salt (I) with the zeolite and the inorganic binder to form the mixture powder:
mixing a metal salt (II) having an amount of a metal component of 0.001~3.0 wt % relative to a zeolite with the zeolite having a molar ratio of silica to alumina of 20~100 to conduct an ion-exchange reaction.

4. The method of producing a catalyst for xylene isomerization according to claim 1, wherein the zeolite is ZSM-5.

5. The method of producing a catalyst for xylene isomerization according to claim 1, wherein the VIII group metal is platinum.

6. The method of producing a catalyst for xylene isomerization according to claim 1, wherein the metal salt (I) is selected from the group consisting of beryllium acetylacetonate, magnesium acetylacetonate, calcium acetylacetonate, barium acetylacetonate, beryllium carbonate, magnesium carbonate, calcium carbonate, and barium carbonate.

7. The method of producing a catalyst for xylene isomerization according to claim 1, wherein an amount of a metal component of the metal salt (I) is 0.1~3.0 wt % based on the total amount of the zeolite.

8. The method of producing a catalyst for xylene isomerization according to claim 3, wherein the metal salt (II) is selected from the group consisting of beryllium nitrate, beryllium halide, beryllium acetate, beryllium citrate, beryllium gluconate, beryllium carbonate, beryllium formate, beryllium sulfate, beryllium hydroxide, magnesium nitrate, magnesium halide, magnesium acetate, magnesium citrate, magnesium gluconate, magnesium carbonate, magnesium formate, magnesium sulfate, magnesium hydroxide, calcium nitrate, calcium halide, calcium acetate, calcium citrate, calcium gluconate, calcium carbonate, calcium formate, calcium sulfate, calcium hydroxide, barium nitrate, barium halide, barium acetate, barium citrate, barium gluconate, barium carbonate, barium formate, barium sulfate, and barium hydroxide.

9. The method of producing a catalyst for xylene isomerization according to claim 3, wherein the ion-exchange reaction is conducted at a temperature of 30~250° C.

10. The method of producing a catalyst for xylene isomerization according to claim 1, wherein the inorganic binder is selected from the group consisting of silica, silica-alumina, alumina, aluminum phosphate, bentonite, kaolin, clinoptilolite, and montmorillonite.

11. A catalyst for xylene isomerization, comprising:
a carrier including a zeolite, having a molar ratio of silica to alumina of 20~100, impregnated with or mixed with a metal salt (I) having an amount of a metal component of 0.05~5.0 wt % relative to a zeolite, and an inorganic binder, in which an amount of the zeolite is 10~90 wt % based on the total amount of the carrier,
wherein the carrier is supported with a VIII group metal such that an amount of the VIII group metal is 0.001~3.0 wt % based on a total amount of the catalyst, or is supported with the VIII group metal additionally supported with tin, bismuth or lead such that an amount of the tin, bismuth or lead is 0.01~5.0 wt % based on the total amount of the catalyst,
the zeolite is selected from the group consisting of ZSM-5, ZSM-8, ZSM-11, ZSM-12, ZSM-23, ZSM-35, ZSM-48, SSZ-46, TS-1, TS-2, mordenite, and Beta, and
the metal salt (I) is selected from the group consisting of beryllium nitrate, beryllium halide, beryllium acetate, beryllium naphthenate, beryllium gluconate, beryllium citrate, beryllium acetylacetonate, beryllium carbonate, beryllium formate, beryllium sulfate, beryllium hydroxide, magnesium nitrate, magnesium halide, magnesium acetate, magnesium naphthenate, magnesium gluconate, magnesium citrate, magnesium acetylacetonate, magnesium carbonate, magnesium formate, magnesium sulfate, magnesium hydroxide, calcium nitrate, calcium halide, calcium acetate, calcium naphthenate, calcium gluconate, calcium citrate, calcium acetylacetonate, calcium carbonate, calcium formate, calcium sulfate, calcium hydroxide, barium nitrate, barium halide, barium acetate, barium naphthenate, barium gluconate, barium citrate, barium acetylacetonate, barium carbonate, barium formate, barium sulfate, and barium hydroxide.

12. A catalyst for xylene isomerization, comprising:
a carrier including a zeolite, having a molar ratio of silica to alumina of 20~100, ion-exchanged with a metal salt (II) having an amount of a metal component of 0.001~3.0 wt % relative to a zeolite, and impregnated with or mixed with a metal salt (I) having an amount of a metal component of 0.05~5.0 wt % relative to a zeolite, and an inorganic binder, in which an amount of the zeolite is 10~90 wt % based on a total amount of the carrier,
wherein the carrier is supported with a VIII group metal such that an amount of the VIII group metal is 0.001~3.0 wt % based on a total amount of the catalyst, or is supported with the VIII group metal additionally supported with tin, bismuth or lead such that an amount of the tin, bismuth or lead is 0.01~5.0 wt % based on the total amount of the catalyst,
the zeolite is selected from the group consisting of ZSM-5, ZSM-8, ZSM-11, ZSM-12, ZSM-23, ZSM-35, ZSM-48, SSZ-46, TS-1, TS-2, mordenite, and Beta;
the metal salt (I) is selected from the group consisting of beryllium nitrate, beryllium halide, beryllium acetate, beryllium naphthenate, beryllium gluconate, beryllium citrate, beryllium acetylacetonate, beryllium carbonate, beryllium formate, beryllium sulfate, beryllium hydroxide, magnesium nitrate, magnesium halide, magnesium acetate, magnesium naphthenate, magnesium gluconate, magnesium citrate, magnesium acetylacetonate, magnesium carbonate, magnesium formate, magnesium sulfate, magnesium hydroxide, calcium nitrate, calcium halide, calcium acetate, calcium naphthenate, calcium gluconate, calcium citrate, calcium acetylacetonate, calcium carbonate, calcium formate, calcium sulfate, calcium hydroxide, barium nitrate, barium halide, barium acetate, barium naphthenate, barium gluconate, barium citrate, barium acetylacetonate, barium carbonate, barium formate, barium sulfate, and barium hydroxide; and
the metal salt (II) is selected from the consistinog beryllium nitrate, beryllium halide, beryllium acetate, beryllium citrate, beryllium gluconate, beryllium carbonate, beryllium formate, beryllium sulfate, beryllium hydroxide, magnesium nitrate, magnesium halide, magnesium acetate, magnesium citrate, magnesium gluconate, magnesium carbonate, magnesium formate, magnesium sulfate, magnesium hydroxide, calcium nitrate, calcium halide, calcium acetate, calcium citrate, calcium gluconate, calcium carbonate, calcium formate, calcium sulfate, calcium hydroxide, barium nitrate, barium halide, barium acetate, barium citrate, barium gluconate, barium carbonate, barium formate, barium sulfate, and barium hydroxide.

* * * * *

UNITED STATES PATENT AND TRADEMARK OFFICE
CERTIFICATE OF CORRECTION

PATENT NO.      : 8,030,239 B2
APPLICATION NO. : 12/312361
DATED           : October 4, 2011
INVENTOR(S)     : Oh et al.

It is certified that error appears in the above-identified patent and that said Letters Patent is hereby corrected as shown below:

On the Title page, Item (73) should read

(73) Assignee:   SK Innovation Co., Ltd. and SK Global Chemical Co., Ltd.

Signed and Sealed this
Thirtieth Day of October, 2012

David J. Kappos
*Director of the United States Patent and Trademark Office*